(12) United States Patent
Sugimoto

(10) Patent No.: US 9,211,245 B2
(45) Date of Patent: Dec. 15, 2015

(54) COSMETIC COMPOSITION

(71) Applicant: AJINOMOTO CO., INC., Tokyo (JP)

(72) Inventor: Takanori Sugimoto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/497,734

(22) Filed: Sep. 26, 2014

(65) Prior Publication Data

US 2015/0010489 A1  Jan. 8, 2015

Related U.S. Application Data

(63) Continuation of application No. PCT/JP2013/060563, filed on Mar. 29, 2013.

(30) Foreign Application Priority Data

Mar. 30, 2012 (JP) ................. 2012-080379

(51) Int. Cl.
| | |
|---|---|
| *A61K 8/49* | (2006.01) |
| *A61K 8/368* | (2006.01) |
| *A61K 8/34* | (2006.01) |
| *A61Q 19/00* | (2006.01) |
| *A61K 8/73* | (2006.01) |

(52) U.S. Cl.
CPC ................ *A61K 8/4913* (2013.01); *A61K 8/34* (2013.01); *A61K 8/368* (2013.01); *A61K 8/73* (2013.01); *A61K 8/737* (2013.01); *A61Q 19/00* (2013.01); *A61K 2800/10* (2013.01); *A61K 2800/524* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,093,109 | A * | 3/1992 | Mausner | 424/63 |
| 6,156,077 | A * | 12/2000 | Shibata et al. | 8/406 |
| 2002/0037559 | A1 | 3/2002 | Sauter et al. | |
| 2006/0099166 | A1 * | 5/2006 | Vandeputte | 424/70.13 |
| 2006/0229291 | A1 | 10/2006 | Straetmans et al. | |
| 2008/0153839 | A1 * | 6/2008 | Cotton et al. | 514/252.12 |
| 2008/0200534 | A1 * | 8/2008 | Roso et al. | 514/423 |
| 2010/0055062 | A1 * | 3/2010 | Arditty | 424/70.7 |

FOREIGN PATENT DOCUMENTS

| | | |
|---|---|---|
| CN | 1213400 A | 3/1997 |
| DE | 102 33 339 A1 | 11/2003 |
| JP | 10-81607 A | 3/1998 |
| JP | 2001/207188 A | 7/2001 |
| JP | 2005-289873 A | 10/2005 |
| JP | 2008-143903 A | 6/2008 |
| JP | 2010/510284 A | 4/2010 |
| WO | WO 03/089394 A2 | 10/2003 |

OTHER PUBLICATIONS

SciFinder, N-acyl proline, retrieved online on Mar. 31, 2015.*
JP 2005-289873, Partial Human Translation of Paragraph 0014, 2005.*
International Search Report issued Jul. 2, 2013 in PCT/JP2013/060563.
U.S. Appl. No. 14/584,310, filed Dec. 29, 2014, Sugimoto, et al.
Extended European Search Report dated Sep. 28, 2015 issued in EP 13768097, 6 pages.
A. Tungler et al: "Enantioselective hydrogenation of [alpha]-[beta]-unsaturated ketones", Catalysis Today, vol. 5, No. 2, Apr. 1, 1989, pp. 159-171.
Chinese Office Action and English translation issued in Chinese application No. 2015083101546040, 9 pages.

* cited by examiner

*Primary Examiner* — Jennifer A Berrios
(74) *Attorney, Agent, or Firm* — Oblon, McClelland, Maier & Neustadt, L.L.P.

(57) ABSTRACT

Provided is a composition that masks the odor characteristic of anisic acid or phenylalkanol, is superior in appearance and texture on application, and provides moist feeling to the skin after application. Specifically, a composition containing (A) acyl proline represented by the formula (I) or a salt thereof, and (B) one or more kinds selected from anisic acid and phenylalkanol is provided.

14 Claims, No Drawings

COSMETIC COMPOSITION

CROSS REFERENCES TO RELATED APPLICATIONS

This application is a continuation of International Patent Application No. PCT/JP2013/060563, filed on Mar. 29, 2013, and claims priority to Japanese Patent Application No. 2012-080379 filed on Mar. 30, 2012, both of which are incorporated herein by reference in their entireties.

BACKGROUND OF THE INVENTION

1. Field of the Invention

The present invention relates to a composition containing (A) particular acyl proline or a salt thereof, and (B) one or more kinds selected from anisic acid and phenylalkanol. Furthermore, the present invention relates to a composition containing, in addition to the above-mentioned (A), (B), (C) a water-soluble polymer and/or (D) polyvalent alcohol.

2. Discussion of the Background

In recent years, out of concern for the environment, there is much demand for cosmetics using natural components. Specifically, cosmetics using plant-derived starting materials are highly popular.

Anisic acid is a plant-derived starting material known to have an antibacterial power (patent document 1), and its application to cosmetics is known (patent document 2).

DOCUMENT LIST

Patent Documents

[patent document 1] JP-A-10-81607
[patent document 2] US-B-2006-0229291

SUMMARY OF THE INVENTION

Problems to be Solved by the Invention

However, anisic acid has a characteristic odor and, when it is added to a cosmetic in expectation of its antibacterial power alone, masking of the odor is desired. Moreover, the water-holding capacity of the skin may be impaired by anisic acid. In addition, cosmetic agents containing anisic acid tend to show a decrease in the gloss (appearance), and texture on application. Thus, a method that solves such problems by the addition of a plant-derived starting material has been desired. Phenylalkanols such as phenethyl alcohol, phenylpropanol and the like also have similar problems. Therefore, the problem of the present invention is to provide a composition that masks the odors characteristic of anisic acid and phenylalkanol, is superior in the appearance and texture on application, and provides moist feeling to the skin after application.

Means of Solving the Problems

In view of such situation, the present inventor has conducted intensive studies and found that the above-mentioned problems are solved by a combined use of particular acyl proline and anisic acid and/or phenylalkanol, which resulted in the completion of the present invention.

Accordingly, the present invention includes the following embodiments.

[1] A composition comprising
(A) acyl proline represented by the formula (I):

wherein an acyl group represented by $R^1$—CO— is an acyl group derived from a saturated or unsaturated fatty acid having 2-23 carbon atoms, or a salt thereof, and
(B) one or more kinds selected from anisic acid and phenylalkanol.

[2] The composition of the above-mentioned [1], wherein, in acyl proline represented by the formula (I), the acyl group represented by $R^1$—CO— is an acyl group derived from a saturated or unsaturated fatty acid having 6-12 carbon atoms.

[3] The composition of the above-mentioned [1] or [2], wherein acyl proline represented by the formula (I) is decanoyl proline.

[4] The composition of any one of the above-mentioned [1]-[3], wherein (A) is contained in 0.001 wt %-5 wt % relative to the total amount of the composition.

[5] The composition of any one of the above-mentioned [1]-[4], wherein (A) is contained in 0.01 wt %-2 wt % relative to the total amount of the composition.

[6] The composition of any one of the above-mentioned [1]-[5], wherein (B) is one or more kinds selected from anisic acid, phenylmethanol, phenethyl alcohol and phenylpropanol.

[7] The composition of any one of the above-mentioned [1]-[6], wherein (B) is anisic acid or phenethyl alcohol.

[8] The composition of any one of the above-mentioned [1]-[7], wherein (B) is anisic acid.

[9] The composition of any one of the above-mentioned [1]-[8], wherein (B) is contained in 0.001 wt %-5 wt % relative to the total amount of the composition.

[10] The composition of any one of the above-mentioned [1]-[9], wherein (B) is contained in 0.05 wt %-1 wt % relative to the total amount of the composition.

[11] The composition of any one of the above-mentioned [1]-[10] wherein the weight of (A)/the weight of (B) is 99/1-1/99.

[12] The composition of any one of the above-mentioned [1]-[11], further comprising (C) a water-soluble polymer.

[13] The composition of the above-mentioned [12], wherein (C) is at least one selected from the group consisting of xanthan gum, guar gum, locust bean gum and carageenan.

[14] The composition of any one of the above-mentioned [1]-[13], further comprising (D) polyvalent alcohol.

[15] The composition of the above-mentioned [14], wherein (D) is at least one selected from the group consisting of glycerin, 1,3-butylene glycol and 1,3-propanediol.

[16] A cosmetic agent comprising the composition of any one of the above-mentioned [1]-[15].

[17] A method of preparing a composition comprising one or more kinds selected from anisic acid and phenylalkanol, comprising a step of mixing acyl proline represented by the formula (I):

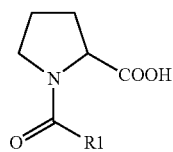

wherein the acyl group represented by $R^1$—CO— is an acyl group derived from a saturated or unsaturated fatty acid having 2-23 carbon atoms, or a salt thereof, and one or more kinds selected from anisic acid and phenylalkanol, whereby masking an odor characteristic of anisic acid or phenylalkanoyl.

[17-2] The method of the above-mentioned [17], wherein, in acyl proline represented by the formula (I), the acyl group represented by $R^1$—CO— is an acyl group derived from a saturated or unsaturated fatty acid having 6-12 carbon atoms.

[17-3] The method of the above-mentioned [17], wherein acyl proline represented by the formula (I) is decanoyl proline.

[17-4] The method of the above-mentioned [17], wherein acyl proline represented by the formula (I) is added at a proportion of 0.001 wt %-5 wt % relative to the total weight of the composition.

[17-5] The method of the above-mentioned [17], wherein acyl proline represented by the formula (I) is added at a proportion of 0.01 wt %-2 wt % relative to the total weight of the composition.

[18] Use of acyl proline represented by the formula (I):

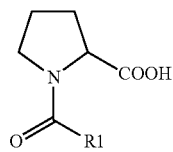

wherein the acyl group represented by $R^1$—CO— is an acyl group derived from a saturated or unsaturated fatty acid having 2-23 carbon atoms, or a salt thereof, for masking an odor characteristic of anisic acid or phenylalkanol.

[18-2] The use of the above-mentioned [18], wherein, in acyl proline represented by the formula (I), the acyl group represented by $R^1$—CO— is an acyl group derived from a saturated or unsaturated fatty acid having 6-12 carbon atoms.

[18-3] The use of the above-mentioned [18], wherein acyl proline represented by the formula (I) is decanoyl proline.

[18-4] The use of the above-mentioned [18], wherein acyl proline represented by the formula (I) is added at a proportion of 0.001 wt %-5 wt % relative to the total weight of the composition.

[18-5] The use of the above-mentioned [18], wherein acyl proline represented by the formula (I) is added at a proportion of 0.01 wt %-2 wt % relative to the total weight of the composition.

Effect of the Invention

According to the present invention, a composition that masks odor(s) characteristic of one or more kinds selected from anisic acid and phenylalkanol, is superior in the appearance and texture on application, and provides moist feeling to the skin after application can be obtained.

In the present specification, the "odor(s) characteristic of one or more kinds selected from anisic acid and phenylalkanol" means smell(s) exclusively of anisic acid and/or phenylalkanol itself/themselves. The "masking" means that the smell exclusively of a substance by itself is made to be unscented by reducing the odor or changing the quality of the odor.

DETAILED DESCRIPTION OF THE PREFERRED EMBODIMENTS

The composition of the present invention contains (A) particular acyl proline or a salt thereof, and (B) one or more kinds selected from anisic acid and phenylalkanol.

[(A) Acyl Proline]

The acyl proline in the present invention is represented by the formula (1).

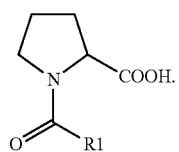

An acyl group represented by $R^1$—CO— is an acyl group derived from a saturated or unsaturated fatty acid having 2-23 carbon atoms. Examples thereof include an acetyl group, an isopropanoyl group, a propanoyl group, a butanoyl group, an isobutanoyl group, a sec-butanoyl group, a tert-butanoyl group, a pentanoyl group, a sec-pentanoyl group, a tert-pentanoyl group, an isopentanoyl group, a hexanoyl group, a heptanoyl group, an octanoyl group, a 2-ethylhexanoyl group, a tert-octanoyl group, a nonanoyl group, an isononanoyl group, a decanoyl group, an isodecanoyl group, an undecanoyl group, a lauroyl group, an undecylenoyl group, a myristoyl group, a palmitoyl group, a stearoyl group, a behenoyl group and an oleoyl group. A long chain acyl group represented by $R^1$—CO— may be, besides an acyl group derived from an acid having a single composition, an acyl group derived from a naturally-obtained mixed fatty acid such as coconut oil fatty acid, castor oil fatty acid, olive oil fatty acid, palm oil fatty acid and the like, or a fatty acid obtained by synthesis (including branched fatty acid). One of these may be used, or two or more kinds selected from the above-mentioned group may be mixed for use. The acyl group represented by $R^1$—CO— is preferably an acyl group derived from a saturated or unsaturated fatty acid having 4-18 carbon atoms, more preferably an acyl group derived from a saturated or unsaturated fatty acid having 6-12 carbon atoms, further preferably an acyl group derived from a saturated or unsaturated fatty acid having 8-10 carbon atoms, and further preferably a decanoyl group.

Therefore, $R^1$ in the formula is a hydrocarbon group having 1-22 carbon atoms. Examples of the "hydrocarbon group" include chain hydrocarbon groups such as an alkyl group, an alkynyl group and the like. A chain hydrocarbon group is preferable, and both straight chain and branched chain can be used. An alkyl group is more preferable, which more preferably has 3-17, more preferably 5-11, more preferably 7-9, carbon atoms.

Examples of the salt of the compound of the formula (1) include alkali metal salts such as lithium salt, sodium salt, potassium salt and the like; alkaline earth metal salts such as calcium salt, magnesium salt and the like; ammonium salts such as alkanolamine salt and the like; basic organic substance salt and the like. Of these, sodium salt, potassium salt and ammonium salt are preferable, sodium salt and potassium salt are more preferable, and sodium salt is further preferable, from the aspect of solubility.

The production method of acyl proline of the present invention is not particularly limited, and acyl proline can be easily produced by combining known methods. Specifically, acyl proline can be prepared from proline and acid chloride using the Schotten-Baumann method including simultaneous dropwise addition of acid chloride and a base such as sodium hydroxide and the like. The proline may be an L form, a D form or a mixture thereof, preferably an L form.

The amount of acyl proline to be added in the present invention is preferably 0.001 wt %-5 wt %. The lower limit is more preferably 0.01 wt %, further preferably 0.05 wt %. From the aspect of texture of the composition on application, the upper limit is more preferably 4 wt %, more preferably 3 wt %, more preferably 2 wt %, more preferably 1.5 wt %, further preferably 1 wt %, and furthermore preferably 0.5 wt %.

[(B) Anisic Acid or Phenylalkanol]

The anisic acid in the present invention is also called methoxybenzoic acid, which is an organic compound wherein benzene is substituted by a carboxyl group and a methoxy group. Examples thereof include p-anisic acid (4-methoxybenzoic acid), m-anisic acid (3-methoxybenzoic acid) and o-anisic acid (2-methoxybenzoic acid).

In addition, examples of phenylalkanol in the present invention include a substance having a hydroxyalkyl group on the benzene ring. Examples of the hydroxyalkyl group include a hydroxyalkyl group having 1-10 carbon atoms, preferably a hydroxyalkyl group having 1-6 carbon atoms, more preferably a hydroxyalkyl group having 1-3 carbon atoms, more preferably a hydroxyalkyl group having 2-3 carbon atoms.

Specific examples thereof include phenylmethanol, phenethyl alcohol (also called 2-phenylethanol) and 3-phenylpropanol. These components can be used singly as component (B), or two or more kinds thereof may be used in combination.

From the aspect of antiseptic effect, anisic acid or phenethyl alcohol is preferable, anisic acid is more preferable, and p-anisic acid (4-methoxybenzoic acid) is more preferable.

The anisic acid in the present invention can be prepared by synthesis, and can also be obtained by extracting from a suitable plant. Out of concern for the environment, anisic acid extracted from a plant is preferable. It is also possible to commercially obtain same as "Dermosoft 688 ECO" (Dr. Streatmans).

Similarly, phenylalkanol in the present invention can be prepared by synthesis, and can also be obtained from a plant-derived starting material. Phenethyl alcohol can be prepared by synthesis, and can also be obtained from a plant-derived starting material. It is also possible to commercially obtain same as "Dermosoft PEA ECO" (Dr. Streatmans). In addition, phenylpropanol can be prepared by synthesis and can also be prepared by reducing from a plant-derived starting material. (patent document: DE10233339)

The amount of the anisic acid or phenylalkanol to be added in the composition of the present invention is preferably 0.001 wt %-5 wt %. The lower limit is more preferably 0.01 wt %, further preferably 0.05 wt %, since a composition free of an odor problem and having superior antiseptic property can be obtained. On the other hand, the upper limit is preferably 2 wt %, more preferably 1.5 wt %, further preferably 1 wt %, still more preferably 0.5 wt %, from the aspect of texture of the composition on application.

The weight of (A)/the weight of (B) is preferably 99/1-1/99, the upper limit is preferably 98/2, more preferably 97/3, further preferably 95/5, more preferably 90/10, more preferably 85/15, from the aspects of texture on application and appearance. The lower limit is preferably 2/98, more preferably 5/95, more preferably 10/90, more preferably 15/85, more preferably 40/60, more preferably 50/50, from the aspect of antiseptic effect.

The composition of the present invention preferably contains (C) a water-soluble polymer in addition to the above-mentioned (A) and (B), from the aspect of texture on application.

[(C) Water-Soluble Polymer]

The water-soluble polymer of the present invention may be a synthetic polymer, but is preferably obtained from a naturally occurring substance. Examples of the water-soluble polymer include guar gum, locust bean gum, quince seed, carageenan, galactan, gum arabic, gum tragacanth, pectin, mannan, starch, xanthan gum, dextran, succinoglucan, curdlan, hyaluronic acid, gelatin, casein, albumin, collagen, methylcellulose, ethylcellulose, hydroxyethylcellulose, carboxymethyl cellulose, methyl hydroxypropyl cellulose, soluble starch, carboxymethyl starch, methyl starch, alginic acid propylene glycol ester, alginates, polyvinyl alcohol, polyvinylpyrrolidone, polyvinyl methyl ether, carboxyvinyl polymer, sodium polyacrylate, polyethylene oxide, ethylene oxide/propylene oxide copolymer and the like. From the aspect of sustainability, natural polymers such as xanthan gum, guar gum, locust bean gum, carageenan and the like are desirable.

The amount of the water-soluble polymer to be added in the present invention is preferably 0.001 wt %-5 wt %. The lower limit is preferably 0.01 wt %, more preferably 0.1 wt %, from the aspect of texture on application. The upper limit is preferably 2 wt %, more preferably 1.5 wt %, further preferably 1 wt %, still more preferably 0.7 wt %, from the aspect of texture on application.

The composition of the present invention preferably contains (D) polyvalent alcohol in addition to the above-mentioned (A) and (B), from the aspect of moist feeling.

[(D) Polyvalent Alcohol]

Examples of the polyvalent alcohol in the present invention include glycerin, ethylene glycol, 1,3-butylene glycol, 1,3-propanediol, propylene glycol, isoprene glycol and the like. Out of concern for the environment and from the aspect of moist feeling, glycerin, 1,3-butylene glycol and 1,3-propanediol are desirable.

The amount of polyvalent alcohol to be added in the present invention is preferably 0.1 wt %-20 wt %. The lower limit is preferably 0.3 wt %, more preferably 0.5 wt %, more preferably 1 wt %, from the aspect of texture on application. The upper limit is more preferably 15 wt %, further preferably 10 wt %, still more preferably 7 wt %, from the aspect of texture on application.

The composition of the present invention can be added to various cosmetics. Examples thereof include skin care cosmetics such as face washes, skin lotions, skin milks, creams, gels, beauty essence, facial mask, mask sheets, and the like, make-up cosmetics such as white face powder, foundations, lipsticks, cheek colors, eyeliners, mascaras, eyeshadows, pencils and the like, hair-care cosmetics such as shampoos, rinses, hair conditioners, hair styling agents, hair treatments and the like, and body-care cosmetics such as soaps, body shampoos and the like.

The cosmetic agent may contain a component that can be generally added to cosmetic agents as long as the effect of the present invention is not inhibited. Specific examples thereof include oil solutions, chelating agents, surfactants, powders, amino acids, polyamino acids and a salt thereof, sugar alcohol and alkylene oxide adducts thereof, lower alcohols, animal and plant extracts, nucleic acids, vitamins, enzymes, anti-inflammatory agents, antimicrobial agents, preservatives, antioxidants, UV absorbers, adiaphoretics, pigments, dyes, oxidative dyes, organic and inorganic powders, pH adjusters, pearly sheen agents, wetting agents and the like.

Examples of the oil solution include higher alcohols such as cetyl alcohol, isostearyl alcohol, lauryl alcohol, hexadecyl alcohol, octyldodecanol and the like; fatty acids such as isostearic acid, undecylenoic acid, oleic acid and the like; esters such as myristyl myristate, hexyl laurate, decyl oleate, isopropyl myristate, hexyldecyl dimethyl octanoate, glycerine monostearate, diethyl phthalate, ethylene glycol monostearate, octyl oxystearate, benzoic acid alkyl ester and the like; hydrocarbons such as liquid paraffin, polyisobutene, petrolatum, squalane and the like; wax such as lanolin, reduced lanolin, carnauba wax and the like; fats and oils such as mink oil, cacao oil, coconut oil, palm kernel oil, camellia oil, sesame oil, castor oil, olive oil and the like; cooligomers of ethylene and α-olefin, and the like.

A particular example of the silicone oil is silicone oil selected from the group consisting of ether-modified silicone such as methylpolysiloxane, polymeric methylpolysiloxane, polyoxyethylene/methylpolysiloxane copolymer, polyoxypropylene/methylpolysiloxane copolymer and poly(oxyethylene, oxypropylene)/methylpolysiloxane copolymer and the like, cyclic silicone such as stearoxymethylpolysiloxane, stearoxytrimethylsilane, methylhydrogen polysiloxane, decamethylcyclopentasiloxane, octamethylcyclotetrasiloxane, tetrahydrotetramethylcyclotetrasiloxane, methylcyclopolysiloxane, dodecamethylcyclohexasiloxane and the like; amino-modified silicone such as methylphenylpolysiloxane, trimethylsiloxysilicate, aminoethylaminopropylsiloxane/dimethylsiloxane copolymer and the like, silanol-modified polysiloxane, alkoxy-modified polysiloxane, fatty acid-modified polysiloxane, fluorine-modified polysiloxane, epoxy-modified polysiloxane, alkoxy-modified polysiloxane perfluoropolyether, polyvinyl acetate dimethyl polysiloxane, and mixtures thereof.

While the chelating agent is not particularly limited, preferable examples thereof include a chelating agent selected from the group consisting of triethylenetetramine, 2-thenoyltrifluoroacetone, thioglycolic acid, tartaric acid, succinic acid, 8-quinolinol, pyridine-2,6-dicarboxylic acid, pyridine, 1,10-tenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone and a salt thereof, and mixtures thereof and the like.

Examples of the surfactant include anionic surfactants such as N-long chain acylamino acid salt (N-long chain acyl acidic amino acid salt, N-long chain acyl neutral amino acid salt and the like), N-long chain fatty acid acyl-N-methyl taurate, alkyl sulfate and an alkylene oxide adduct thereof, fatty acid amide ether sulfate, metal salt and weak base salt of fatty acid, sulfosuccinate surfactant, alkylphosphate and an alkylene oxide adduct thereof, alkyl ether carboxylic acid and the like; ether-type surfactant (glycerine ether and an alkylene oxide adduct thereof and the like), ester-type surfactant (glycerine ester and an alkylene oxide adduct thereof and the like), ether ester-type surfactant (sorbitan ester and an alkylene oxide adduct thereof and the like), ester-type surfactant (polyoxyalkylene fatty acid ester, glycerine ester, fatty acid polyglycerine ester, sorbitan ester, sucrose fatty acid ester and the like), alkylglucosides, nitrogen-containing non-ionic surfactants (hydrogenated castor oil pyroglutamic acid diester and an ethylene oxide adduct thereof, fatty acid alkanolamide and the like), cationic surfactants such as aliphatic amine salt (alkylammonium chloride, dialkylammonium chloride and the like), quaternary ammonium salt thereof, aromatic quaternary ammonium salt (a benzalkonium salt and the like), fatty acid acyl arginine ester and the like; amphoteric surfactant such as betaine-type surfactant (carboxybetaine and the like), aminocarboxylic acid-type surfactant, imidazoline-type surfactant and the like, and the like.

Examples of the powder include resin powder such as nylon beads, silicone beads and the like, nylon powder, metal fatty acid soap, yellow iron oxide, red iron oxide, black iron oxide, chromium oxide, cobalt oxide, carbon black, ultramarine, iron blue, zinc oxide, titanium oxide, zirconium oxide, silicon oxide, aluminum oxide, cerium oxide, titanated mica, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, fine particles of titanium oxide, fine particles of zinc oxide, fine particles of iron oxide, acyl amino acid such as acyl lysine, acylglutamic acid, acylarginine, acylglycine and the like and the like. Furthermore, surface treatment such as silicone treatment, fluorine compound treatment, silane coupling agent treatment, silane treatment, organic titanate treatment, acylated lysine treatment, fatty acid treatment, metallic soap treatment, oil solution treatment, amino acid treatment and the like may be applied.

Examples of the amino acid include glycine, alanine, serine, threonine, arginine, glutamic acid, aspartic acid, isoleucine, leucine, valine and the like.

Examples of the polyamino acid and a salt thereof include polyglutamic acid, polyaspartic acid and the like.

Examples of the sugar alcohol and an alkylene oxide adduct thereof include mannitol and the like.

Examples of the lower alcohol include ethanol, propanol and the like.

EXAMPLES

While the present invention is now explained in more detail by referring to the Examples, the present invention is not limited to the following Examples.

Synthetic Example 1

Synthesis of Decanoyl Proline

Proline (manufactured by Ajinomoto Co., Inc., 34.54 g) was dissolved in water (100 g), and decanoyl chloride (manufactured by Tokyo Chemical Industry Co., Ltd., 52.01 g) and 25% aqueous sodium hydroxide solution were added while adjusting to pH 12. The mixture was neutralized with 75% sulfuric acid, and the aqueous layer was removed. Water and ethyl acetate were further added, and the aqueous layer was removed. Ethyl acetate was evaporated under reduced pressure to give decanoyl proline (68.12 g).

Synthetic Example 2

Synthesis of Decanoyl Proline Sodium Salt

Decanoyl proline obtained in Synthetic Example 1 was suspended in a suitable amount of water, and the suspension was neutralized with sodium hydroxide to pH 5 to give a decanoyl proline sodium salt.

Synthetic Example 3

Synthesis of Lauroyl Proline

Using proline and lauroyl chloride, and by a method similar to that in Synthetic Example 1, lauroyl proline was synthesized.

Synthetic Example 4

Synthesis of Lauroyl Proline Sodium Salt

Using proline and lauroyl chloride, and by a method similar to that in Synthetic Example 2, a lauroyl proline sodium salt was synthesized.

<Evaluation of the Composition of the Present Application>

A cream was prepared at the blending amounts shown in Table 1 and Table 2, and the following evaluation was performed. The cream was prepared by dissolving each of component I and component II by heating at 85° C., adding II to I by small portions, and cooling the mixture to room temperature.

TABLE 1

|   | component | amount blended (%) |
|---|---|---|
| I | squalane | 5.0 |
|   | jojoba oil | 5.0 |
|   | stearyl alcohol | 3.8 |
|   | glyceryl stearate | 2.9 |
| II | water | balance |
|   | sucrose palmitate | 0.4 |
|   | sodium stearoyl glutamate | 0.1 |
|   | citrate buffer | q.s. |
|   | component (A) | described in Table 2 |
|   | component (B) | described in Table 2 |
|   | component (C) | described in Table 2 |
|   | component (D) | described in Table 2 |

[Evaluation 1: Masking of Odor]

Five professional panelists made evaluation according to the following evaluation criteria.
4 points: odor characteristic of anisic acid or phenylalkanoyl was not felt at all
3 points: odor characteristic of anisic acid or phenylalkanol was scarcely felt
2 points: odor characteristic of anisic acid or phenylalkanol was slightly felt
1 point: odor characteristic of anisic acid or phenylalkanol was felt
0 point: odor characteristic of anisic acid or phenylalkanol was clearly felt
Average points of the professional panelists:
⊚: not less than 3.0 points, ○: not less than 2.0 points and less than 3.0 points, Δ: not less than 1.5 points and less than 2.0 points, ×: less than 1.5 points
In advance, the panelists were made to recognize the odors of anisic acid (manufactured by Tokyo Chemical Industry Co., Ltd.), phenethyl alcohol (Dermosoft PCA ECO (manufactured by Dr. Streatmans)) and phenylpropanol (manufactured by Tokyo Chemical Industry Co., Ltd.)) as an odor characteristic of anisic acid or phenylalkanol.

[Evaluation 2: Appearance]

The appearance of the prepared composition was evaluated by five professional panelists according to the following evaluation criteria.
4 points: high gloss was felt
3 points: gloss was felt
2 points: slight gloss was felt
1 point: gloss was scarcely felt
0 point: gloss was not felt at all
Average points of the professional panelists:
⊚: not less than 3.5 points, ○: not less than 2.5 points and less than 3.5 points, Δ: not less than 1.5 points and less than 2.5 points, ×: less than 1.5 points

[Evaluation 3: Spreadability on Application]

The spreadability on application of the prepared composition was evaluated by five professional panelists according to the following evaluation criteria.
4 points: high spreadability was felt on application
3 points: spreadability was felt on application
2 points: slight spreadability was felt on application
1 point: spreadability was scarcely felt on application
0 point: spreadability was not felt at all on application
Average points of the professional panelists:
⊚: not less than 3.5 points, ○: not less than 2.5 points and less than 3.5 points, Δ: not less than 1.5 points and less than 2.5 points, ×: less than 1.5 points

[Evaluation 4: Compatibility on Application]

The compatibility on application of the prepared composition was evaluated by five professional panelists according to the following evaluation criteria.
4 points: high compatibility was felt on application
3 points: compatibility was felt on application
2 points: slight compatibility was felt on application
1 point: compatibility was scarcely felt on application
0 point: compatibility was not felt at all on application
Average points of the professional panelists:
⊚: not less than 3.5 points, ○: not less than 2.5 points and less than 3.5 points, Δ: not less than 1.5 points and less than 2.5 points, ×: less than 1.5 points

[Evaluation 5: Freshness on Application]

The freshness on application of the prepared composition was evaluated by five professional panelists according to the following evaluation criteria.
4 points: high freshness was felt on application
3 points: freshness was felt on application
2 points: slight freshness was felt on application
1 point: freshness was scarcely felt on application
0 point: freshness was not felt at all on application
Average points of the professional panelists:
⊚: not less than 3.5 points, ○: not less than 2.5 points and less than 3.5 points, Δ: not less than 1.5 points and less than 2.5 points, ×: less than 1.5 points

[Evaluation 6: Moist Feeling after Application]

The moist feeling immediately after application of the prepared composition was evaluated by five professional panelists according to the following evaluation criteria.
4 points: high moist feeling was felt on application
3 points: moist feeling was felt on application
2 points: slight moist feeling was felt on application
1 point: moist feeling was scarcely felt on application
0 point: moist feeling was not felt at all on application
Average points of the professional panelists:
⊚: not less than 3.5 points, ○: not less than 2.5 points and less than 3.5 points, Δ: not less than 1.5 points and less than 2.5 points, ×: less than 1.5 points

TABLE 2

| component | | Ex. 1 | Ex. 2 | Ex. 3 | Ex. 4 | Ex. 5 | Ex. 6 | Ex. 7 | Ex. 8 |
|---|---|---|---|---|---|---|---|---|---|
| A | compound of Synthetic Example 2 (decanoyl proline Na) | 2.00 | 0.50 | 0.50 | 0.50 | 0.50 | 0.50 | 0.50 | 0.10 |
| B | anisic acid phenethyl alcohol phenylpropanol | 0.10 | 0.10 | 0.10 | 0.10 | 0.10 | 0.10 | 0.10 | 0.10 |
| C | xanthan gum | | | 0.20 | 0.80 | | 0.20 | | |
| D | glycerin | | | | | 3.00 | 3.00 | 15.00 | |
| | water | balance | balance | balance | balance | balance | balance | balance | balance |
| | total | 100 | 100 | 100 | 100 | 100 | 100 | 100 | 100 |
| | A/B | 95/5 | 83/17 | 83/17 | 83/17 | 83/17 | 83/17 | 83/17 | 50/50 |
| evaluation | masking of odor | ◎ | ○ | ○ | ○ | ○ | ○ | ○ | ○ |
| | appearance | ○ | ○ | ○ | ○ | ○ | ○ | ○ | ○ |
| | spreadability on application | ○ | ○ | ◎ | ◎ | ○ | ◎ | ◎ | ○ |
| | compatibility on application | ◎ | ○ | ○ | ○ | ◎ | ◎ | ◎ | ○ |
| | freshness on application | ○ | ○ | ◎ | ◎ | ◎ | ◎ | ◎ | ○ |
| | moist feeling after application | Δ | ○ | ◎ | ◎ | ◎ | ◎ | Δ | ○ |

| component | | Ex. 9 | Ex. 10 | Ex. 11 | Comp. Ex. 1 | Comp. Ex. 2 | Comp. Ex. 3 |
|---|---|---|---|---|---|---|---|
| A | compound of Synthetic Example 2 (decanoyl proline Na) | 0.01 | 0.50 | 0.50 | | | |
| B | anisic acid phenethyl alcohol phenylpropanol | 0.05 | 0.10 | 0.10 | 0.10 | 0.10 | 0.10 |
| C | xanthan gum | | | | | | |
| D | glycerin | | | | | | |
| | water | balance | balance | balance | balance | balance | balance |
| | total | 100 | 100 | 100 | 100 | 100 | 100 |
| | A/B | 17/83 | 83/17 | 83/17 | — | — | — |
| evaluation | masking of odor | Δ | ○ | ○ | X | X | X |
| | appearance | ○ | ○ | ○ | X | X | X |
| | spreadability on application | ○ | ○ | ○ | X | X | X |
| | compatibility on application | Δ | ○ | ○ | X | X | X |
| | freshness on application | ○ | ○ | ○ | X | X | X |
| | moist feeling after application | Δ | ○ | ○ | X | X | X |

The compositions of the Examples were superior in all the evaluated items as compared to Comparative Examples not containing (A).

Formulation Example 1

Preparation of Moisturizing Cream

A moisturizing cream with the following formulation was prepared according to a conventional method.

TABLE 3

| | (mass %) |
|---|---|
| compound of Synthetic Example 2 (decanoyl proline sodium) | 0.50 |
| anisic acid | 0.12 |
| squalane | 5.00 |
| jojoba oil | 5.00 |
| macadamia nut oil | 5.00 |
| caprylic/capric triglyceride | 5.00 |
| di(phytosteryl/octyldodecyl)lauroyl glutamate | 1.00 |
| isostearyl hydroxystearate | 2.00 |
| shea butter | 2.00 |
| stearyl alcohol | 3.80 |
| carnauba wax | 0.10 |
| glyceryl stearate | 2.90 |
| xanthan gum | 0.20 |
| sucrose palmitate | 0.40 |

TABLE 3-continued

| | (mass %) |
|---|---|
| sodium stearoyl glutamate | 0.10 |
| citrate buffer | q.s. |
| water | balance |
| | 100.00 |

The obtained moisturizing cream was a composition that masks an odor characteristic of anisic acid, is superior in appearance and texture on application, and provides moist feeling to the skin after application.

Preparation Example 2

Preparation of Skin Lotion

A skin lotion with the following formulation was prepared according to a conventional method.

TABLE 4

| | (mass %) |
|---|---|
| compound of Synthetic Example 4 (lauroyl proline sodium) | 0.20 |
| anisic acid | 0.05 |
| di(phytosteryl/octyldodecyl)lauroyl glutamate | 0.35 |
| cetyl octanoate | 0.15 |
| PPG-8 ceteth-20 | 0.50 |
| PPG-6 decyltetradeceth-30 | 0.50 |
| glycerin | 1.25 |
| water | 5.00 |
| DPG | 2.00 |
| BG | 3.00 |
| citrate buffer | q.s. |
| water | balance |
| | 100.00 |

The obtained skin lotion was a composition that masks an odor characteristic of anisic acid, is superior in appearance and texture on application, and provides moist feeling to the skin after application.

The detail of the materials used is as follows.
squalane: squalane (Maruha Nichiro Corporation)
jojoba oil: purified jojoba oil (KOEI KOGYO Co., Ltd.)
stearyl alcohol: KALCOL 8688 (Kao Corporation
glyceryl stearate: NIKKOL GMS-BV2 (Nikko Chemicals Co., Ltd.)
sucrose palmitate: SURFHOPE SE COSME C-1615 (Mitsubishi-Kagaku Foods Corporation)
sodium stearoyl glutamate: "AMISOFT" HS-11P (Ajinomoto Co., Inc.)
xanthan gum: KELTROL CG-T (Sansho Co., Ltd.)
macadamia nut oil: macadamia nut oil (Nikko Chemicals Co., Ltd.)
caprylic/capric triglyceride: TCG-M (Kokyu Alcohol Kogyo Co., Ltd.)
di(phytosteryl/octyldodecyl)lauroyl glutamate: "ELDEW" PS-203 (Ajinomoto Co., Inc.)
isostearyl hydroxystearate: SCHERCEMOL SHS Ester (GSI Creos Corporation)
shea butter: SHEA BUTTER RF (Kokyu Alcohol Kogyo Co., Ltd.)
carnauba wax: purified carnauba wax (CERARICA NODA Co., Ltd.)
PPG-8 ceteth-20: NIKKOL PBC-44 (Nikko Chemicals Co., Ltd.)
PPG-6 decyltetradeceth-30: PEN-4630 (Nikko Chemicals Co., Ltd.)

INDUSTRIAL APPLICABILITY

It is significant that an odor characteristic of anisic acid or phenylalkanoyl is masked by using the particular composition of the present invention, and a cosmetic agent having a sufficient antiseptic effect can be provided.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic composition, comprising:
(A) at least one acyl proline represented by formula (I):

$$\text{(I)}$$

wherein $R^1$—CO— is an acyl group derived from a saturated or unsaturated fatty acid having 4 to 18 carbon atoms, or a salt thereof; and
(B) one or more compounds selected from the group consisting of anisic acid, phenylmethanol, phenethyl alcohol and phenylpropanol,
wherein the content of (A) based on the total weight of the composition is from 0.01 wt % to 5 wt %, and the content of (B) based on the total weight of the composition is from 0.05 wt %-1 wt %.

2. A cosmetic composition according to claim 1, wherein $R^1$—CO— is an acyl group derived from a saturated or unsaturated fatty acid having 6 to 12 carbon atoms.

3. A cosmetic composition according to claim 1, wherein said acyl proline represented by formula (I) is decanoyl proline.

4. A cosmetic composition according to claim 2, wherein said acyl proline represented by formula (I) is decanoyl proline.

5. A cosmetic composition according to claim 1, which comprises 0.01 wt % to 2 wt %, based on the total weight of the composition, of (A) said acyl proline represented by formula (I).

6. A cosmetic composition according to claim 1, wherein (B) is anisic acid or phenethyl alcohol.

7. A cosmetic composition according to claim 1, wherein (B) is anisic acid.

8. A cosmetic composition according to claim 1, wherein said (A) and said (B) are present in a weight ratio, weight of (A)/weight of (B), of 99/1 to 1/99.

9. A cosmetic composition according to claim 1, further comprising:
(C) at least one water-soluble polymer.

10. A cosmetic composition according to claim 9, wherein (C) is at least one member selected from the group consisting of xanthan gum, guar gum, locust bean gum, and carageenan.

11. A cosmetic composition according to claim 1, further comprising:
(D) at least one polyvalent alcohol.

12. A cosmetic composition according to claim 11, wherein (D) is at least one member selected from the group consisting of glycerin, 1,3-butylene glycol, and 1,3-propanediol.

13. A method of preparing a cosmetic composition comprising one or more compounds selected from the group consisting of anisic acid, phenylmethanol, phenethyl alcohol and phenylpropanol,
said method comprising mixing:
(A) at least one acyl proline represented by formula (I):

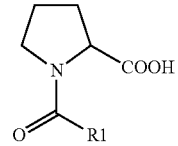

(I)

wherein $R^1$—CO— is an acyl group derived from a saturated or unsaturated fatty acid having 4 to 18 carbon atoms, or a salt thereof, with
(B) one or more compounds selected from the group consisting of anisic acid, phenylmethanol, phenethyl alcohol and phenylpropanol,
thereby masking an odor characteristic of anisic acid, phenylmethanol, phenethyl alcohol and phenylpropanol,
wherein the content of (A) based on the total weight of the composition is from 0.01 wt % to 5 wt %, and the content of (B) based on the total weight of the composition is from 0.05 wt %-0.7 wt %.

14. A method for masking an odor characteristic of anisic acid, phenylmethanol, phenethyl alcohol and phenylpropanol, comprising adding:
(A) at least one acyl proline represented by formula (1):

(I)

wherein $R^1$—CO— is an acyl group derived from a saturated or unsaturated fatty acid having 4 to 18 carbon atoms, or a salt thereof,
to a cosmetic composition comprising:
(B) one or more compounds selected from the group consisting of anisic acid, phenylmethanol, phenethyl alcohol and phenylpropanol,
wherein the content of (A) based on the total weight of the composition is from 0.01 wt % to 5 wt %, and the content of (B) based on the total weight of the composition is from 0.05 wt %-0.7 wt %.

* * * * *